United States Patent [19]
Gonon et al.

[11] Patent Number: 6,083,189
[45] Date of Patent: Jul. 4, 2000

[54] BIFUNCTIONAL LIQUID DISPENSING GENERATOR, IN PARTICULAR FOR STERILIZED LIQUIDS

[75] Inventors: Bertrand Gonon, Lyons; Alain Sezeur, Cachan, both of France

[73] Assignee: Saphir Medical, Lyons, France

[21] Appl. No.: 09/202,682

[22] PCT Filed: Jun. 20, 1997

[86] PCT No.: PCT/FR97/01108

§ 371 Date: Feb. 24, 1999

§ 102(e) Date: Feb. 24, 1999

[87] PCT Pub. No.: WO97/49441

PCT Pub. Date: Dec. 31, 1997

[30] Foreign Application Priority Data

Jun. 21, 1996 [FR] France .................................. 96/07907

[51] Int. Cl.[7] .................................................. A61M 1/00
[52] U.S. Cl. .............................. 604/19; 604/118; 604/131
[58] Field of Search ................................. 604/19, 21, 22, 604/30, 31, 32, 118, 121, 131, 132, 133, 149, 245–247

[56] References Cited

U.S. PATENT DOCUMENTS

| | | | |
|---|---|---|---|
| 2,669,233 | 2/1954 | Friend | 128/251 |
| 3,963,024 | 6/1976 | Goldowsky | 128/214 R |
| 4,457,487 | 7/1984 | Steigerwald | 251/117 |
| 4,662,871 | 5/1987 | Rafelson | 604/119 |
| 4,913,698 | 4/1990 | Ito et al. | 604/22 |

FOREIGN PATENT DOCUMENTS

| | | |
|---|---|---|
| 0 411 170 | 7/1989 | European Pat. Off. . |
| 2 454 308 | 11/1980 | France . |
| 37 26 788 A1 | 2/1989 | Germany . |
| 646167 | 11/1950 | United Kingdom . |
| WO 94/27659 | 12/1994 | WIPO . |
| WO 94/28807 | 12/1994 | WIPO . |

OTHER PUBLICATIONS

Japanese Abstract, vol. 013, No. 105 (C–575) dated Mar. 13, 1989 to Sugino Mach:KK and JP 63279832.

*Primary Examiner*—John D. Yasko
*Attorney, Agent, or Firm*—Davis and Bujold

[57] ABSTRACT

The bifunctional generator comprises a closed or self-feeding bag (1) containing the reserve of liquid (2) to be used, the bag being pressure-constrained in a chamber (3) and hydraulically coupled with the supply link (13) of a hand piece (5, 6) by a connecting hydraulic section (9). The pressure generator or delivery generator functioning mode is determined each time by the presence in the connecting section of at least one hydraulic component (19, 21) and/or a hydraulic conformation (20, 22) associated with the particular feature of the hand piece used. This invention is of interest for the manufacturers of medical appliances: aquadissection, resectoscopy, lavage, disinfecting or the like and it as useful applications for various foodstuffs.

26 Claims, 6 Drawing Sheets

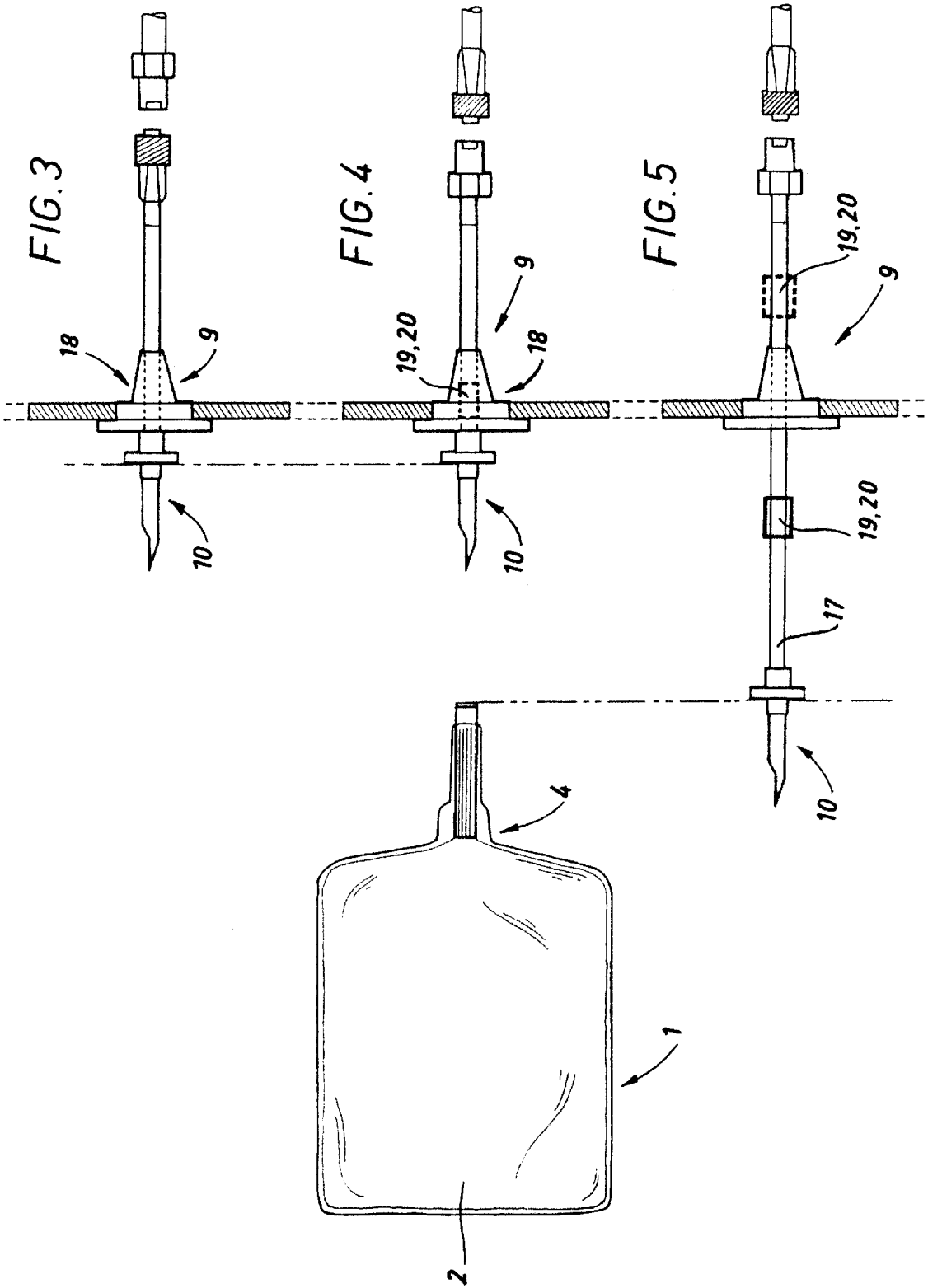

BIFUNCTIONAL LIQUID DISPENSING GENERATOR, IN PARTICULAR FOR STERILIZED LIQUIDS

The purpose of the generator-dispenser is to deliver a liquid, particularly a sterile liquid, at a constant, regulable pressure or at a constant, regulable flow.

One adaptation of the invention delivers sterilized liquid under sterile conditions such as those required in medical applications.

The generator consists of a flexible container placed in a chamber where a predetermined pressure is exerted by an inert, gaseous fluid, preferably a fluid that is immiscible with the liquid in the flexible container. The pressurized gas expels the liquid through a connection piece and a conduit terminating in a hand piece.

BACKGROUND OF THE INVENTION

There are various medical procedures, such as, for example aquadissection, injecting medication or contrast substances, cleansing or lavage of a deep area, disinfecting, and so forth, which must be performed using high pressure.

The pressurized liquid expelled through the end of the hand piece initially needs to be under sufficient pressure from the compression gas, but also requires a high pressure type conduit connecting it with the hand piece and a calibrated outlet opening with a shape and diameter corresponding to the type of spray used for the designated application.

Publication WO 94/28807 of SAPHIR MEDICAL concerns a surgical aquadissection apparatus formed of a physiological serum generator contained in a pouch under pressure in a chamber sealed with pressurized gas and connected to a hand piece by a flexible conduit, which in turn is connected to a circuit leading from the pouch through a sterile pin, penetrating one of the chamber walls through a cone-shaped seal.

A circuit terminating in a hand piece is connected to a suction pump for suctioning the liquid and evacuating fragments tissue produced during the aquadissection procedure.

This invention has a single objective: providing a generator for use in surgical dissection which emits a spray of sterile liquid.

To achieve this objective, the physiological serum must be projected at high pressure that can be regulated manually by the operator.

This is accomplished by maintaining a constant pressure, or incision pressure, at the outlet of the hand piece. An electronic regulating circuit maintains constant pressure in the sealed chamber. As a result, the incision pressure is consistently maintained at the optimal level for the surgery being performed.

Other inventions concerning generators of this type are Publication No.

EP 0 411 170, and U.S. Pat. No. 4,913,698 ITO. These concern the production of a concentrated, high pressure spray for performing aquadissection.

However, there are other instances, such as medical, surgical, and related applications, where the use of high pressure is not advisable. This is the case for pulverization, rinsing, spraying, humidifying, contact disinfection, impregnation, or irrigation with a stream of liquid.

These other applications require a different type of generator, as the procedures require that the liquid not be produced using pressure. On the contrary, a low pressure stream of liquid is desired.

One illustration of a flow generator can be found in Publication No. WO 94/27659 filed by GUIGNARD.

This physiological liquid generator also consists of a pouch holding the liquid, with the pouch subjected to propelling pressure in a sealed chamber. The pressure source is a bottle of neutral gas under pressure. The gas pressure is stringently regulated by a pressure sensor and regulator. A safety valve is adjusted to 30 kPa, or 0.3 bars. This low pressure is appropriate for an endoscopy procedure. It is actually possible to inject only low pressure liquids into the human body.

However, this generator delivers a large volume of liquid, as it also supplies a clarifying liquid for improving visibility in the surgical field. Of course, this liquid is evacuated to eliminate abnormal organ swelling and diffusion of the liquid throughout the body, and a peristaltic extraction pump is provided for this purpose.

This generator has limited pressure and cannot be used in procedures where pressure is required for the procedure, for example, dissection.

It is apparent that the different requirements described above cannot be satisfied by a single generator-dispenser using the same element to connect it with a hand piece which is interchangeable depending upon the function or application.

The goal of the present invention is to provide a single liquid generator-dispenser used in two alternating functions or modes, which eliminates slow, labor-intensive manipulations, and affords a high degree of precision under sterile conditions compatible with medical and surgical requirements.

More specifically, the goal of the present invention is to achieve a bifunctional, multi-purpose, sterile generator-dispenser which functions both as a pressure generator and a delivery generator with only one simple modification.

Yet another goal of the invention is to furnish a sterile, bifunctional generator which can function as either a pressure generator or a delivery generator depending upon either the connecting element selected, preferably a disposable element, or the control exerted on a hydraulic component, thus ensuring that it remains sterile, providing a bifunctional device at far less cost than a device with two juxtaposed functions.

SUMMARY OF THE INVENTION

The invention relates to a sterile generator-distributor for supplying liquid which is either sterile or will be sterilized, contained a flexible, closed or-self-feeding pouch, containing a reserve of liquid under pressure in a chamber, comprising a connecting section penetrating one wall of the chamber between the pouch and a zone connecting it with the supply conduit which furnishes liquid to a hand piece used to inject, spray, project, or otherwise apply the fluid, wherein the connecting section and/or the hand piece have a hydraulic component or adaptor used to transform the generator-distributor from a pressure generator to a delivery generator, depending upon whether the hydraulic component is used and the placement of that component.

The generator-distributor offers many advantages not only in the medical and surgical professions, but also in various other fields requiring highly sterile conditions, such as the food industry.

Thus, by merely changing the connecting section, which is preferably a single-use element, and interposing either a hydraulic component, which may already be incorporated in that element or in the connecting piece, or by including hydraulic adaptor, the pressure generator can be transformed into a delivery generator, or vice versa, for use in a different application.

All the conventional advantages of both a bifunctional apparatus and an apparatus with an integrated supplemental function are inherent in this invention. In addition, switching from one function to the other is accomplished very simply.

Besides the uses outlined above, the following specific medical and surgical applications are cited as examples:

When used as a pressure generator:
at low and medium pressure (from 0 to 5 bars): injecting liquid medication, using spray to cleanse wounds . . .
at higher pressure (greater than 5 bars): aquadissection, injecting drugs or contrast substances with a catheter, removing embedded particles from a deep wound . . .

When used as a delivery generator, at flow rates that can be adjusted from 0 to 3 L/mn:
cleansing of surgical and peritoneum areas;
endoscopic irrigation.

In surgery, especially surgery of the digestive tract, one specific use for the generator of the invention is to use a stream of high pressure physiological serum for dissection in both conventional surgery and laparoscopy and also, without changing the generator, to cleanse the peritoneum during laparoscopy.

The pressure or the flow rate are established at a constant but regulable value determined by the control button. This value can be modified during the course of the manipulation or the procedure.

BRIEF DESCRIPTION OF THE DRAWINGS

Other characteristics and features of the invention will be obvious from the following description, given by way of example, and the accompanying drawings, in which:

FIGS. 3, 4, and 5 are plan views showing three examples of connectors, two with one piece cone-pins and flexible exterior connectors, and one with a connecting section, in a pressure generator (FIG. 3) and a flow generator (FIGS. 4 and 5), respectively;

DESCRIPTION OF THE PREFERRED EMBODIMENTS

Figure 1:
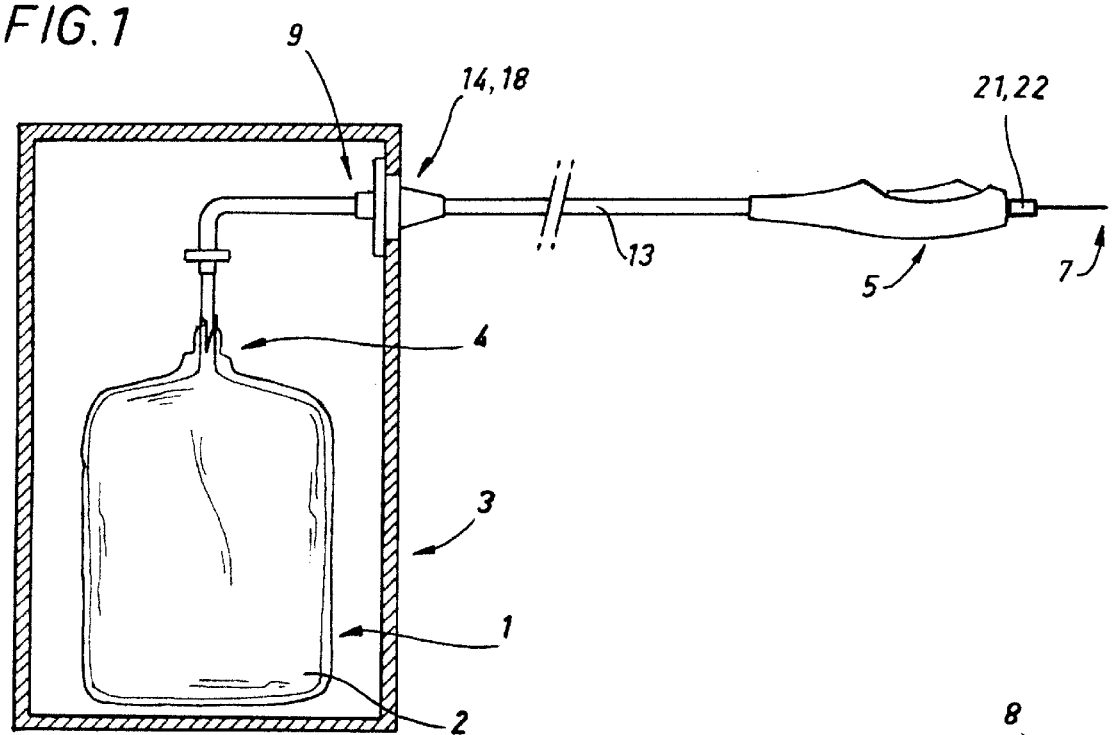
FIG. 1 is a schematic plan view of the unit showing the generator and its flexible container of liquid for distribution in a pressure generator assembly.
Figure 2:
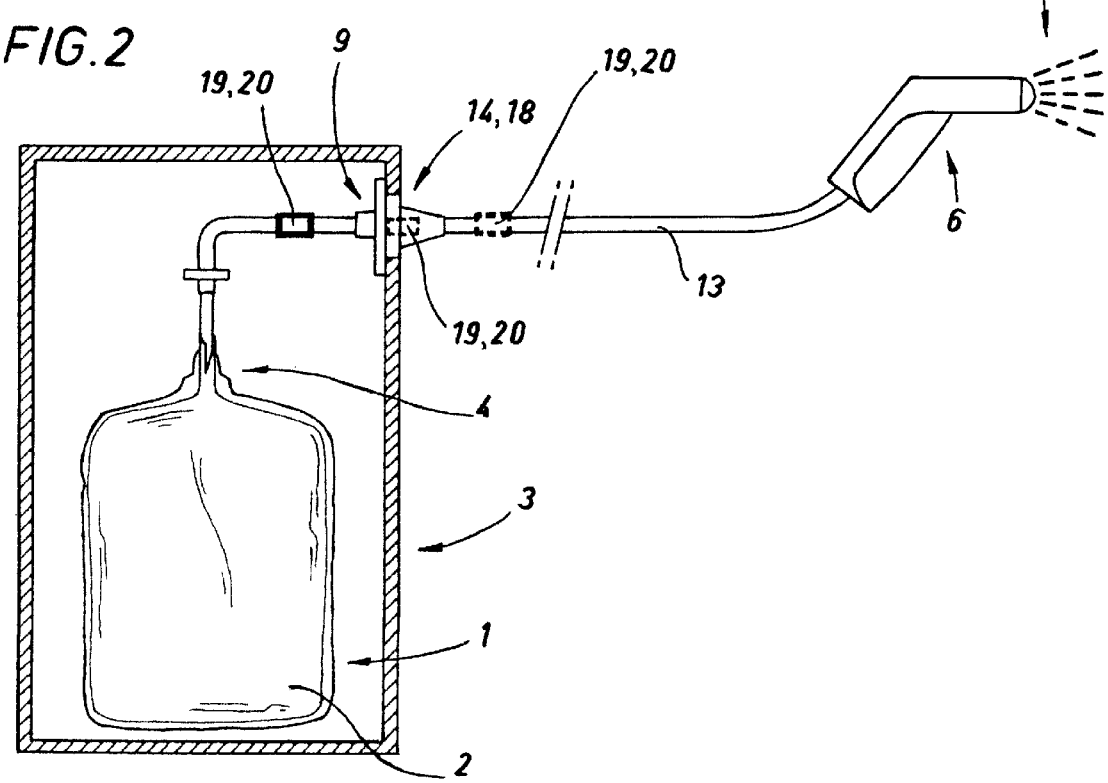
FIG. 2 is a schematic plan view of the unit showing the generator and its flexible container of liquid for distribution in a delivery generator assembly which supplies a generally constant stream of liquid, showing three possible placements of the hydraulic component or hydraulic adaptor.
Figure 6:
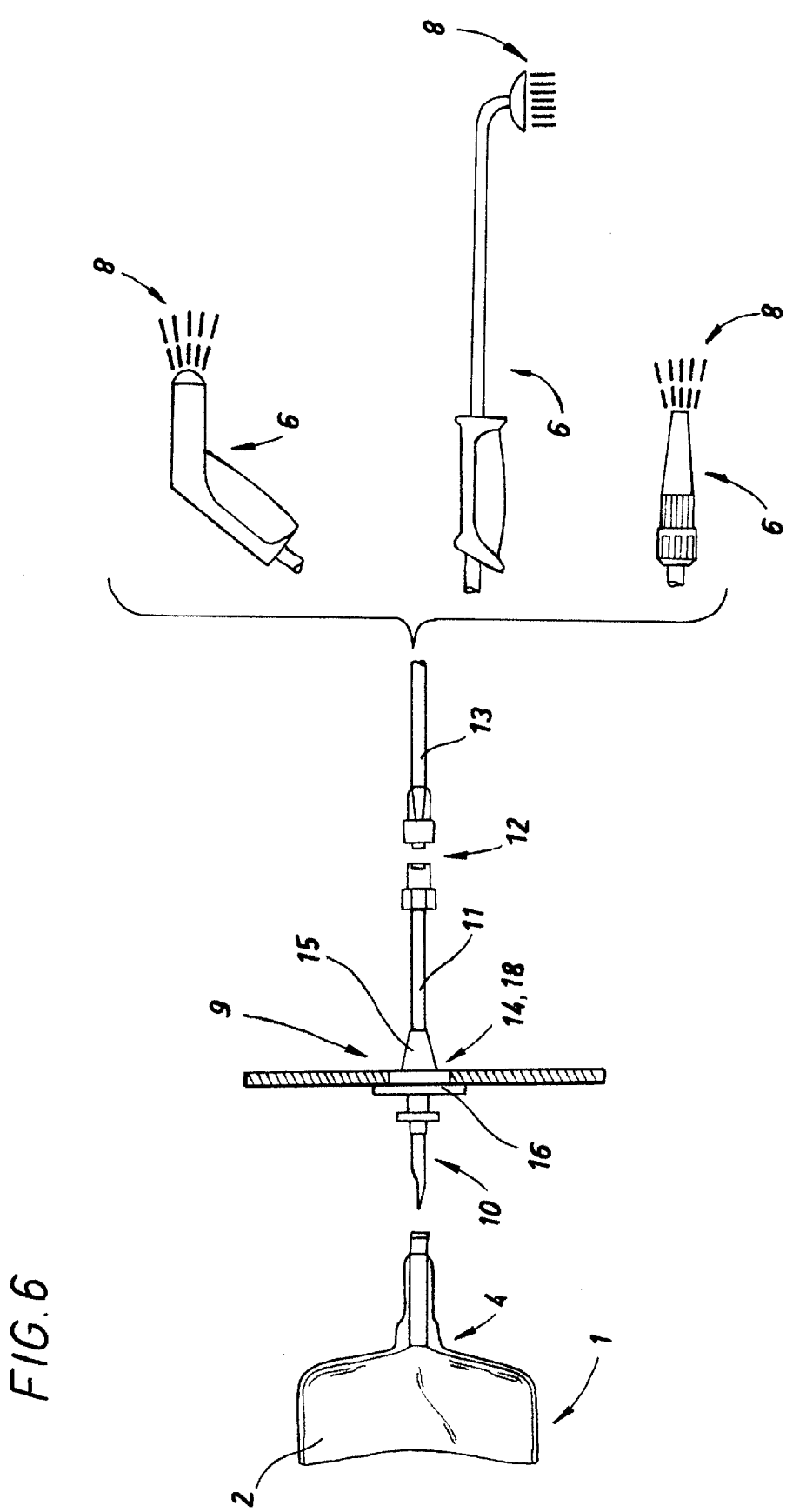
FIG. 6 is a plan view showing a flow generator application with several examples of hand pieces.
Figure 7:
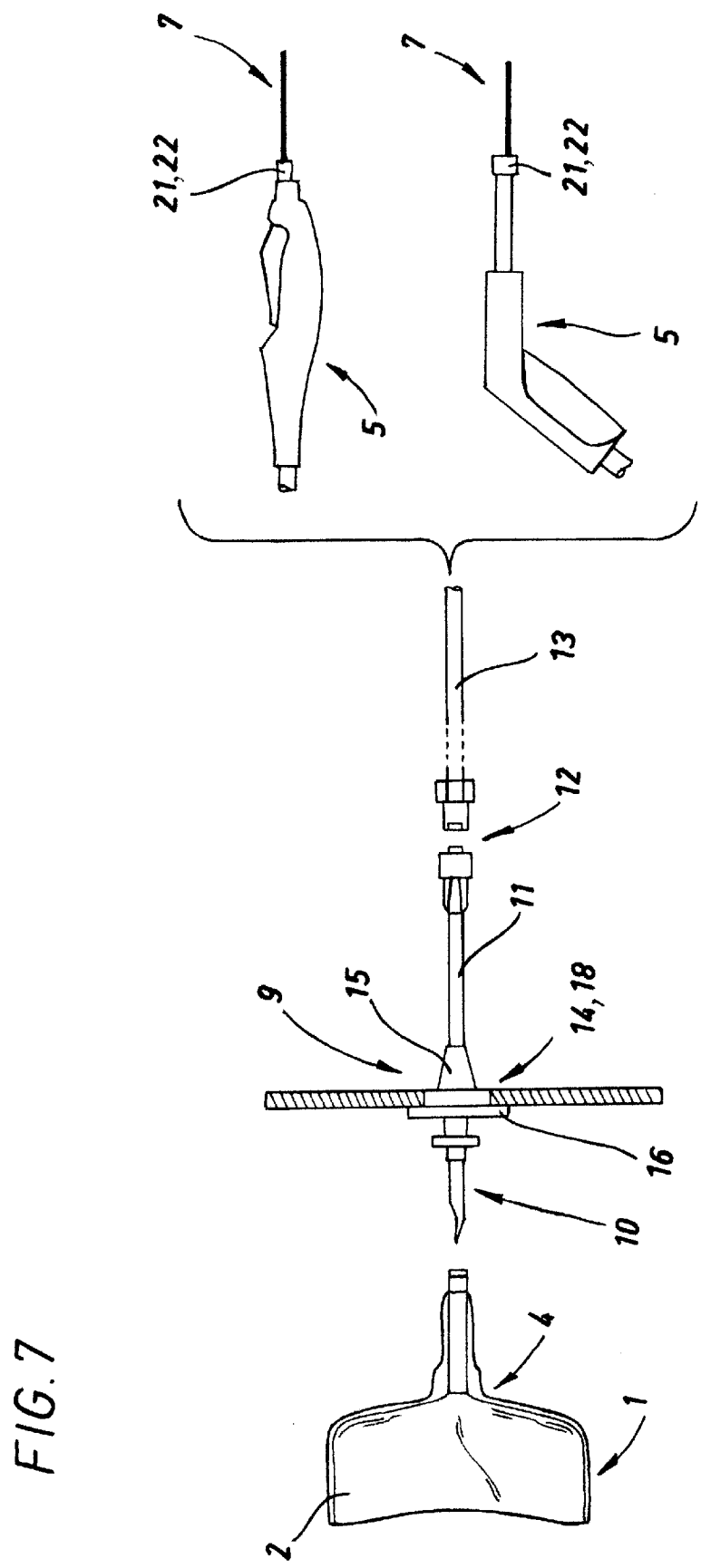
FIG. 7 is a plan view showing a pressure generator application with several examples of hand pieces.

The present invention concerns a generator-distributor, preferably sterile, for supplying liquid, also preferably sterile, from a flexible pouch placed in a chamber where it is subjected to pressure from propelling gas. Said flexible pouch is connected to a hand piece by means of the following elements: a hydraulic connector section formed of a pin followed by a piece passing through the chamber and a connection outside the chamber terminating in an element with a flexible supply inlet supplying the hand piece.

In the sterile version, all the pieces constituting the generator and the generator itself are either sterile or have been sterilized.

The basic inventive principle of the apparatus is that the hydraulic section joining the flexible container to the exterior connection is either partially or totally replaced by another connector, preferably a sterile, disposable one, each time the generator is transformed from a pressure generator to a delivery generator and vice versa, or that the hydraulic section comprises at least one hydraulic component allowing it to switch from one function to the other.

The generator-distributor functioning as a pressure generator or a delivery generator consists of a flexible container 1, for example a pouch, preferably sterile, filled with some sort of liquid 2, also preferably sterile. The pouch is enclosed in a sealed chamber 3 pressurized by a propelling gas, preferably an inert gas which is immiscible with the liquid to be distributed, for example, nitrogen.

It is assumed that the exterior means of pressurizing the chamber are known.

Said sterile pouch 1, filled with a sterile liquid, for example, physiological liquid for a medical or surgical application, has a narrow neck outlet 4, terminating in a tip sealed at the end by an operculum that will be punctured during use.

The generator-distributor of the invention uses one simple modification or control to alternately supply liquid under essentially constant but regulable pressure to a hand piece, either in a pressurized stream 5 or a distributed stream 6, said hand piece varying essentially in form and function depending upon the application.

Pressure hand piece 5 delivers a compact pressurized spray 7, allowing the pressurized spray to be used for the work, while stream delivery hand piece 6 furnishes a diffused spray 8 for other purposes requiring a larger volume of liquid.

Depending upon the application, but especially in medical and surgical procedures, the liquid or solution may be heated up to a certain temperature which is maintained and regulated so that it does not cool the surgical field.

The hydraulic connection between pouch 1 and the exterior consists of a hydraulic connecting section 9 terminating in a pin 10 at one end with a bisected extremity perforating the operculum, and at the other end, following flexible outlet conduit 11, a hydraulic connector 12 with a supply inlet 13 to hand piece 5, 6, after passing through the adjacent wall of the chamber through a passageway in seal 14 housed in an opening in the wall. This sealing element simultaneously seals the interior gas under pressure and the outside. Sealing element 14 has a central opening admitting the conduit of connecting section 9.

As indicated, said connecting section 9 has a fairly short flexible exterior portion 11 connecting it to a hydraulic portion 12 formed of two pieces, for hydraulic connection, preferably at a constant diameter, with hydraulic supply element 13 of hand piece 5, 6.

Sealing element 14 may have a cone-shaped portion 15, with a disc shaped base 16 pressing against the interior wall of the chamber, while the conical extremity has a larger diameter than the opening in the chamber wall and forms a seal by pressing against the edges of the opening and tightly enclosing the outlet conduit.

Connecting section 9 may also have an interior connection 17 between the pin 10 and seal 14.

In the preferred embodiment illustrated in the majority of the drawings, the internal portion of section 9 connecting the wall and flexible pouch 1 which holds liquid 2 is compactly designed. Said internal portion is actually a single piece, which will hereinafter be called the cone-pin 18 in this preferred embodiment. This single element can fulfill all the technical functions of connecting section 9.

In the case of a delivery generator, a hydraulic component 19 and/or a hydraulic adaptor 20, for example, a simple inlet with a calibrated opening, is inserted in or adapted to some portion of the connecting section.

In the case of a pressure generator, a hydraulic component 21 and/or a restricting-type hydraulic adaptor 22, for example, a simple inlet with a calibrated orifice of smaller diameter than the supply connection, is inserted in or adapted immediately on the outlet of pressurizing hand piece 5, while the hydraulic conduit has no restricted connection.

Said hydraulic component or adaptor is integrated with, or adapted to, the single cone-pin element 18 in the embodiment with this single piece. It may consist of a conduit with a precise diameter (calibrated orifice), depending upon the application and the range of generally constant flow speeds desired.

To obtain an extensive range of flow rates, the diameter of this calibrated opening would be generally equal to the diameter of the supply conduit or conduits. Then hand piece 6 for the fluid stream delivery function would be used, that is, a hand piece with an unrestricted outlet.

To obtain a smaller or more restricted range of flow rates, a calibrated orifice of smaller diameter would be used.

The orifice, when integral with or adapted to the single piece, is selected at the time the installation is placed in service.

According to one particular feature of the invention, when in use as a pressure generator, the calibrated passageway providing a generally constant flow may remain only when its diameter is adequate, that is, close to the diameter of the connecting conduits. However, the hand piece must have a narrowed extremity 22, for example, a calibrated orifice considerably smaller than the connecting conduits.

The sectional shape of this calibrated orifice depends upon the application it is designed for. It may be a circular opening designed to create a needle spray for fine surgical applications, or a slit forming a sheet of spray for pressure cleaning procedures.

Depending upon the type of application, connecting section 9 and/or flexible supply connector 13, and/or connector 12, are single use items to conform with standards of sterility in the medical profession and food industry.

It is certainly possible to reuse connecting sections 9 and supply connections 13.

To avoid errors when connecting the elements that determine how the generator functions, connectors 12 may have different shapes. The shapes would represent either the pressure or the stream delivery function. For example, there could be a male connector 12 on the chamber side in the case of a pressure generator, and the reverse in the case of a delivery generator, as shown in FIGS. 3 through 5.

It is also possible to provide for the delivery function and the pressure function at least one neutral hydraulic component which can be adjusted from an operative position to an inoperative position, or progressively controlled to have progressively larger or progressively smaller openings.

For example, the hydraulic component limiting flow, when it has a constricted portion, may become fully passable, that is, fully open, with a simple control. The liquid stream generator-distributor can also be transformed into a pressure generator using a simple exterior control.

To obtain the full effect, it is only necessary to connect the flexible outlet conduit to a specific hand piece which requires sufficient liquid pressure in order to function or fully ensure its function.

As shown in the drawings, an aquadissection instrument has been used as a specific example.

The inventive feature consists of alternately using the same basic apparatus as both a delivery generator and a pressure generator and vice versa, under sterile conditions compatible with medical requirements.

It is also possible, according to a more complex variation of the invention, to switch from one function to the other during the course of a procedure.

Another variation, not shown, consists of replacing the hydraulic component in the flexible exterior portion with a triple track valve, or adding a triple track valve at this location.

The top portion of the generator-distributor must have one or more hydraulic adaptors or components which allow it to function as a stream generator under conditions that are also compatible with its use as a pressure generator.

The three-track component may also incorporate in one element a calibrated stream outlet that may be adjustable.

According to this variation, it is only necessary to connect a pressure hand piece 5 to one of the outlets of the triple track valve and a liquid stream hand piece 6 to its other outlet.

The preferred applications of the apparatus which is the subject the invention are in the medical field, for example, for use in aquadissection (as a pressure generator) or (as a constant liquid stream generator) for injecting substances into the human body, such as contrast substances used prior to radiation, angiograms, or scintigrams, for example.

Certainly, numerous other applications in many varied fields fall within the scope of the invention, especially where sterile conditions are required.

When using the apparatus, it is only necessary to replace the sterile connecting section with another sterile section suitable for the new application.

The generator is a flexible pouch type generator constrained by pressurized inert gas that is not miscible with the fluid to be distributed.

Depending upon the application, it is possible to use other pressurized gases, even air, preferably sterile.

Figure 8:
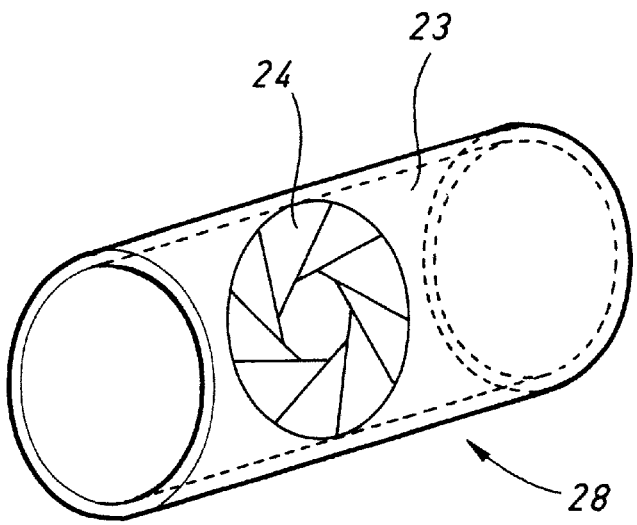
FIG. 8 is a schematic cross-section of a hydraulic piece incorporating a diaphragm, which is remotely controlled.
Figure 9:
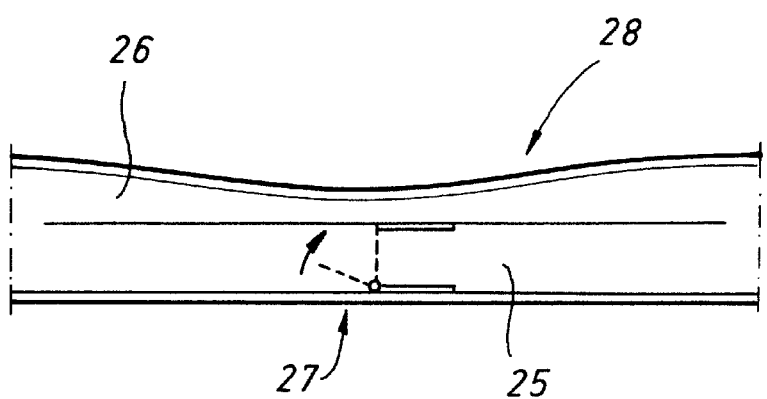
FIG. 9 is a schematic cross-section of a double track hydraulic piece, at least one of which has a remotely controlled block.

As shown in FIGS. 8 and 9, it is even possible to use bi-functional connecting elements, or more generally, bi-functional hydraulic elements, that is, elements whose performance can be controlled, for example, by reducing their size, or more generally, by using constricting devices to reduce their diameter.

In the variation shown in FIG. 8, there is a connecting piece 23 with an integrated diaphragm 24 that is remotely controlled. The diameter of the passageway may be progressively or instantly reduced from being totally open to a smaller calibrated opening for the liquid stream generating function.

In addition, as shown in FIG. 9, there may be a dual track variation, with one large diameter track 25 and one reduced diameter track 26, with a remotely controlled block in at least one track, for example, a valve 27.

It is necessary for there to be a block in large diameter track 25 because reduced diameter track 26, parallel to it, may remain open in the pressure generating mode.

Section 9 may consist of or comprise a flexible portion or a flexible tube 28 made of supple material, for example, an elastic material that can be compressed by transverse or annular squeezing, flattening, or the like, in order to reduce the diameter of the fluid passageway.

Figure 10:
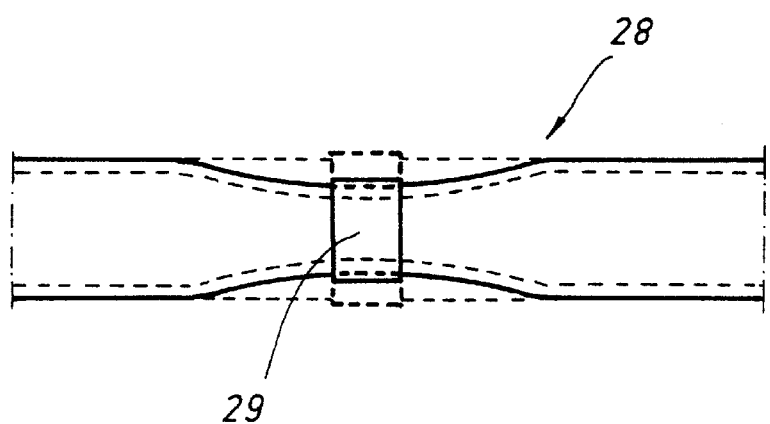
FIG. 10 is a schematic view of a hydraulic piece with the flexible portion constricted by a band.
Figure 11:
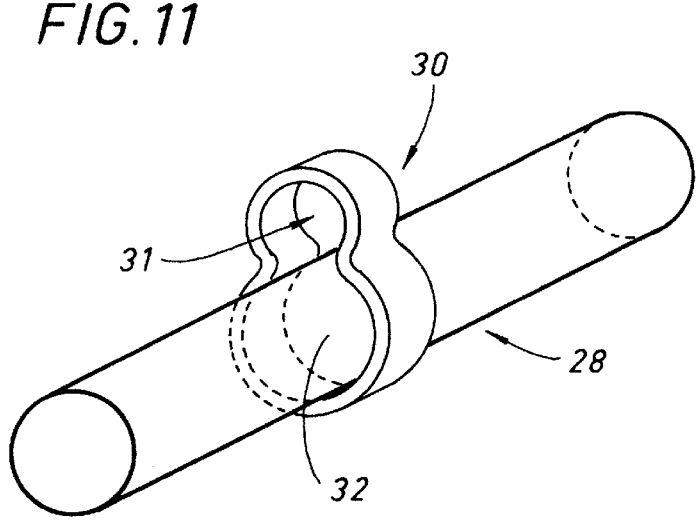
FIG. 11 is a schematic perspective of a hydraulic piece with one portion constricted by an element with a double opening.

This annular compression can be exerted by a band or a deformable annular element 29 (FIG. 10). It may also be exerted by a constricting element 30 with two successive lateral openings 31 and 32, one of which, opening 31, has a diameter equal to the diameter of the flexible portion or flexible tube 28 of the connecting section, and the other, opening 32, having a smaller diameter (FIG. 11). This piece can move transversely along the flexible portion or flexible tube 28 of the section.

Figure 12:
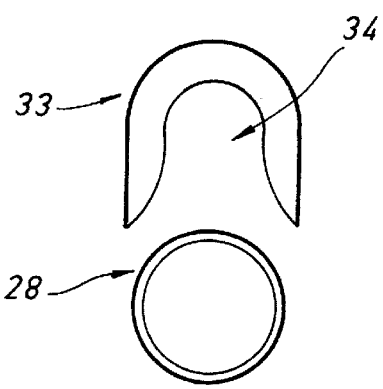
FIG. 12 is a schematic cross-section of a staple-type constricting element.

This constricting element with double openings 31 and 32 may be replaced by a bracket type constricting element 33 with an interior passageway 34 smaller than the diameter of flexible portion 28 of the connecting section (FIG. 12). This bracket element 33 is transversely movable along the flexible portion 28 of the section.

Figure 13:
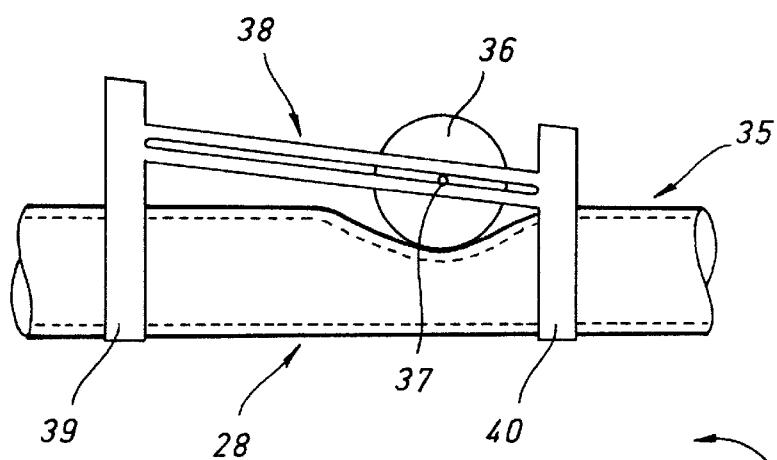
FIG. 13 is a schematic cross-section of a constricting element formed of a wheel on an oblique element.
Figure 14:
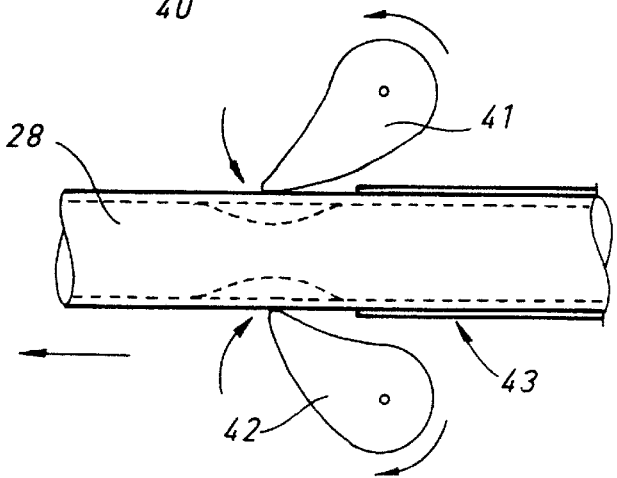
FIG. 14 is a schematic cross-section of a constricting element formed of two pivoting finger clamps.

Other constricting elements may be used to compress, constrain, or flatten the passageway, with the two following devices shown in FIGS. 13 and 14 provided as an example.

The first is constricting element 35 with roller 36 shown in FIG. 13. Device 35 locally flattens the flexible portion 28 of the connecting section by pressing the lateral surface of the roller and the tube or flexible portion 28 against each other. This is done by displacing axle 37 of roller 36 along a descending oblique plane 38. The oblique plane is supported by two transverse end pieces 39 and 40, as shown in FIG. 13.

Next, as shown in FIG. 14, there may be two pivoting finger-like elements 41 and 42 with extremities contacting the lateral surface of the flexible portion 28 of the connecting section, which portion is followed by a rigid area 43. Pivoting fingers 41 and 42 pivot and are each elastically attached, permitting them to move toward each other and against the tube, engaging a catch designed to keep them closed. Displacing the tube in the direction of the arrow prevents it from being gripped by the fingers, as rigid zone 43, which cannot be deformed, is then moved into the area between fingers 41 and 42.

Other elements or adaptors and equivalent devices can certainly be used to make the generator bi-functional.

What is claimed is:

1. A generator-distributor for supplying liquid, particularly sterile liquid, to a hand piece (5) or (6) for surgical or medical applications, which may be either a high pressure or a stream type generator with a closed or self-feeding flexible liquid reserve container sealed inside a chamber by pressurized gas, said container being connected to the exterior by a connecting section (9) with a pin (10) at one end which punctures the lateral wall of the pouch of the flexible container and adapts to the extremity of the pouch, said connecting section (9) penetrating one wall of the chamber through a seal (14) sealing the pressurized gas inside the chamber, while the other end of said section connects with a hand piece (5) or (6) which can function as a high pressure device and a delivery device, respectively, wherein said connecting section (9) penetrating the pressure chamber through seal (14) and supplying the hand piece comprises at least one pressure valve, the presence or absence of which determines whether the generator-distributor functions as a delivery generator or a pressure generator, or vice versa, to the hand piece.

2. A liquid generator-distributor according to claim 1 wherein the connecting section (9) is detachable and may be replaced by a connecting section (9) allowing the other function to take place.

3. A liquid generator-distributor according to claim 2, wherein the connecting section (9) is a single-use element.

4. A liquid generator-distributor according to claim 1, wherein the connecting section (9) is sterile.

5. A liquid generator-distributor according to claim 1, wherein the connecting section (9) comprises a hydraulic pressure valve component.

6. A liquid generator-distributor according to claim 1, wherein the connecting section (9) comprises an interior hydraulic adaptor in the conduit for limiting the pressure of the sterile liquid inside the connecting section (9).

7. A liquid generator-distributor according to claim 5, wherein the connecting section (9) comprises a hydraulic component or a hydraulic adaptor limiting pressure at a location near the wall of the chamber.

8. A liquid generator-distributor according to claim 5, wherein the hydraulic component or the hydraulic adaptor consists of a circular calibrated orifice.

9. A liquid generator-distributor according to claim 1, wherein the hydraulic component or the hydraulic adaptor consists of a constricted area within the conduit passageway located immediately at the end of the connecting section near the hand piece.

10. A liquid generator-distributor according to claim 1, wherein the constricted area consists of a circular calibrated opening or a slit.

11. A liquid generator-distributor according to claims 1, wherein the hydraulic component is a component comprising a calibrated opening located on the connecting section (9).

12. A liquid generator-distributor according to claim 1, wherein the pin (10) and the seal (14) form a single piece called the cone-pin (18).

13. A liquid generator-distributor according to claim 12, wherein the hydraulic component is inside the cone-pin (18) or the cone pin has a hydraulic adaptor.

14. A liquid generator-distributor according to claim 1, wherein the hydraulic component on the section (9) is a triple track valve.

15. A liquid generator-distributor according to claim 14, wherein the triple track valve comprises a hydraulic component or has a hydraulic adaptor determining flow conditions.

16. A liquid generator-distributor according to claim 1, wherein the piece joining the connecting section (9) and the supply inlet (13) to the hand piece is of one type for the pressure generating function and another type for the flow generating function.

17. A liquid generator-distributor according to claim 1, wherein the connecting section (9) comprises two tracks (25) and (26), one of normal diameter and one of reduced diameter, and one of the two tracks has a block (27) that is remotely controlled.

18. A liquid generator-distributor according to claim 17, wherein only the normal diameter comprises a block (27) that is remotely controlled.

19. A liquid generator-distributor according to claim 1, wherein the connecting section (9) either has one portion (28) made of flexible material that can be radially deformed in order to reduce the diameter, or the element consists of a flexible tube (28).

20. A liquid generator-distributor according to claim 19, wherein the diameter of the passageway is reduced by using a constricting element.

21. A liquid generator-distributor according to claim 20, wherein the constriction which reduces the passageway diameter results from attaching a deformable annular element (29) to the flexible tube or the flexible portion (28) of the section.

22. A liquid generator-distributor according to claim 21, wherein the diameter is reduced by using an element with openings.

23. A liquid generator-distributor according to claim 22, wherein the element with openings is a piece (30) with double openings, one large opening (32) and one small opening (31), laterally offset, adapted to the flexible portion (28) of the section and transversely movable along said section.

24. A liquid generator-distributor according to claim 23, wherein the piece with openings is a bracket (33) with branches defining a narrow passageway (34) and forming the constriction.

25. A liquid generator-distributor according to claim 20, wherein the constriction reducing the passageway diameter results from pressure exerted by the lateral surface of a roller (36) against the flexible tube or the flexible portion (28) of the section, said roller rotating on an oblique plane (38).

26. A liquid generator-distributor according to claim 20, wherein the constriction reducing the passageway diameter results from compression by two pivoting fingers (41) and (42) which are pivotably attached and can be elastically forced together towards each other on either side of a flexible portion (28) of the section, followed by a rigid area (43) which can be moved to a position between the fingers when the section is displaced to allow the other function to occur.

* * * * *